United States Patent [19]
Murai et al.

[11] Patent Number: 5,514,811
[45] Date of Patent: May 7, 1996

[54] PROCESS FOR SYNTHESIZING 4-HALO-5-(HYDROXYMETHYL) IMIDAZOLE COMPOUNDS

[75] Inventors: Takayuki Murai; Tokuichi Saeki; Suzuko Satou; Shozo Miura; Tomoko Takashige; Naoki Kano, all of Kagawa, Japan

[73] Assignee: Shikoku Chemicals Corporation, Marugame, Japan

[21] Appl. No.: 195,474

[22] Filed: Feb. 14, 1994

[30] Foreign Application Priority Data

Feb. 15, 1993 [JP] Japan .................................. 5-050190
Sep. 22, 1993 [JP] Japan .................................. 5-259079

[51] Int. Cl.⁶ ................................................ C07D 233/68
[52] U.S. Cl. ................................................ 548/342.5
[58] Field of Search ............................... 548/342.5

[56] References Cited

U.S. PATENT DOCUMENTS 4,577,025  3/1986  Arai et al. ............................. 546/198

OTHER PUBLICATIONS

Watson, S. P., "A Convenient Synthesis of 2—Butyl—4(5)—Chloro—1H—Inidazole—5(4)—Carboxaldeh yde," Synthetic Communications, 22(20), 2971–77 (1992).

Shi, Y. et al., "A Practical Synthesis of 2—Butyl—4(5)—Hydroxymethyl—1H—Imidazole", Synthetic Communications, 23(18), 2623–2630, 1993.

*Primary Examiner*—Jacqueline Haley
*Attorney, Agent, or Firm*—Sherman and Shalloway

[57] ABSTRACT

A process for preparing, on an industrial scale, 4-halo-5-(hydroxymethyl) imidazole compounds that are useful as intermediates for medicines. A 4-chloro-5-(hydroxymethyl) imidazole compound, a 4-bromo-5-(hydroxymethyl) imidazole compound or a like compound is synthesized by reacting a 4,5-bis(hydroxymethyl) imidazole compound with a halogenating agent such as an N-chlorosuccinimide, an N-bromosuccinimide, a chlorinated isocyanuric acid compound or the like compound.

4 Claims, No Drawings

PROCESS FOR SYNTHESIZING 4-HALO-5-(HYDROXYMETHYL) IMIDAZOLE COMPOUNDS

BACKGROUND OF THE INVENTION

1. Field of the Invention

The present invention provides 4-halo-5-(hydroxymethyl) imidazole compounds that are useful as intermediates of medicines such as hypotensive drugs and the like.

The 4-halo-5-(hydroxymethyl) imidazole compound can be converted upon oxidation with manganese dioxide or the like into a 4-halo-5-formylimidazole compound.

2. Description of Prior Art

The 4-halo-5-(hydroxymethyl) imidazole compound has heretofore been synthesized by reacting a 5-(hydroxymethyl) imidazole compound which is a starting material with a halogenating agent such as an N-chlorosuccinimide to halogenate the position 4 of an imidazole ring. For instance, Japanese Patent Publication No. 64428/1988 discloses a 4-chloro-5-(hydroxymethyl) imidazole compound synthesized by the above-mentioned method and having at the position 2 thereof an n-propyl group, an n-butyl group, a t-butyl group, a cyclopentyl group, an m-butoxyphenyl group a p-methylphenyl group, a p-methoxyphenyl group and a p-chlorophenyl group, and Japanese Laid-Open Patent Publication No. 23868/1988 discloses a 4-chloro-5-(hydroxymethyl) imidazole compound having an n-heptyl group and a methoxyethyl group at the position 2 thereof.

The 5-(hydroxymethyl) imidazole compound used as a starting material in the above-mentioned method is prepared by a method of reacting an iminoester compound with a dihydroxyacetone in the liquid ammonia or by a method of reducing a 5-formylimidazole compound with a sodium borohydride. According to the former method, the starting material is handled with difficulty, the reaction apparatus becomes complex, the yield is low and the cost of production is high. The latter method, on the other hand, uses the 5-formylimidazole compound which is an expensive starting material. In either case, therefore, synthesis of the 4-halo-5-(hydroxymethyl) imidazole compound by using the 5-(hydroxymethyl) imidazole compound as a starting material, is not practicable.

SUMMARY OF THE INVENTION

The object of the present invention is to provide a process which is capable of inexpensively mass-producing a 4-halo-5-(hydroxymethyl) imidazole compound by using a 4,5-bis(hydroxymethyl) imidazole compound that is easily obtained by the reaction of an imidazole compound as a starting material with a formaldehyde, and a novel 4-chloro-5-(hydroxymethyl) imidazole compound synthesized by the above process.

Under such circumstances, the present inventors have forwarded the study and have unexpectedly discovered the fact that a 4-halo-5-(hydroxymethyl) imidazole compound represented by the following formula,

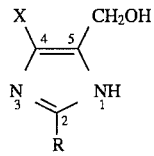

wherein R is a hydrogen atom, an alkyl group, an aryl group or an aralkyl group, and X is a halogen atom, is obtained by reacting a 4,5-bis(hydroxymethyl) imidazole compound with a halogenating agent, and have accomplished the present invention.

DETAILED DESCRIPTION OF PREFERRED EMBODIMENT

According to the present invention, the object 4-halo-5-(hydroxymethyl) imidazole compound is obtained by dissolving a 4,5-bis(hydroxymethyl) imidazole compound in an organic solvent or in water, maintaining the solution at a temperature of 0° to 100° C. and, preferably, at a temperature of 20° to 50° C., adding a halogenating agent to the solution to carry out the reaction for 1 to 24 hours and, preferably, for 2 to 5 hours, concentrating the reaction solution, and refining the concentrated product in a customary manner.

The reaction can be expressed by the following formula,

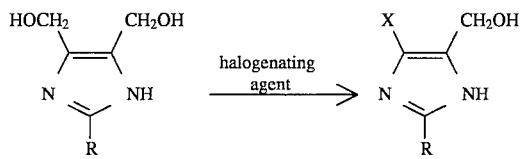

wherein R and X are as defined above.

In refining the 4-halo-5-(hydroxymethyl) imidazole compound according to the process of the present invention, when the 4-halo-5-(hydroxymethyl) imidazole compound which is the object compound is sparingly soluble or insoluble in water, the obtained reaction product is washed with water and is then recrystallized with a suitable solvent to obtain the object product in pure form and, conversely, when the object product is soluble in water, the obtained reaction product is subjected to the column chromatography and is then recrystallized with a suitable solvent to obtain the object product in pure form.

In carrying out the process of the present invention, the halogenating agent may be added to the reaction system at one time or, preferably, in a divided manner or dropwisely. Moreover, the reaction temperature can be lowered and the reaction time can be shortened with a decrease in the molecular weight of the substituent at the position 2 of the starting 4,5-bis(hydroxymethyl) imidazole compound. Conversely, the reactivity decreases with an increase in the molecular weight of the substituent at the position 2, making it necessary to raise the reaction temperature or to lengthen the reaction time.

The 4,5-bis(hydroxymethyl) imidazole compound used as the starting material for the process of the present invention can be prepared by reacting an imidazole compound with twice as much moles of a formaldehyde in an organic solvent such as alcohols or in water in the presence of an alkali catalyst such as sodium hydroxide. This reaction can be represented by the following formula,

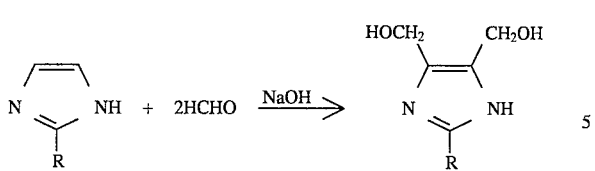

wherein R is as defined above.

Representative examples of the 4,5-bis(hydroxymethyl) imidazole compound that can be used for the process of the present invention include a 4,5-bis(hydroxymethyl) imidazole, a 2-methyl-4,5-bis(hydroxymethyl) imidazole, a 2-ethyl-4,5-bis(hydroxymethyl) imidazole, a 2-propyl-4,5-bis(hydroxymethyl) imidazole, a 2-isopropyl-4,5-bis(hydroxymethyl) imidazole, a 2-butyl-4,5-bis(hydroxymethyl) imidazole, a 2-pentyl-4,5-bis(hydroxymethyl) imidazole, a 2-hexyl-4,5-bis(hydroxymethyl) imidazole, a 2-heptyl-4,5-bis(hydroxymethyl) imidazole, a 2-octyl-4,5-bis(hydroxymethyl) imidazole, a 2-nonyl-4,5-bis(hydroxymethyl) imidazole, a 2-undecyl-4,5-bis(hydroxymethyl) imidazole, a 2-heptadecyl-4,5-bis(hydroxymethyl) imidazole, a 2-phenyl-4,5-bis(hydroxymethyl) imidazole, a 2-paratoluyl-4,5-bis(hydroxymethyl) imidazole, a 2-benzyl-4,5-bis(hydroxymethyl) imidazole, a 2-(1-phenylethyl)-4,5-bis(hydroxymethyl) imidazole, and the like.

Representative examples of the halogenating agent used for the process of the present invention include N-halocarboxylic acid imides such as an N-chlorosuccinimide, an N-bromosuccinimide, etc.; N-halocarboxylic acid amides; halogenated isocyanuric acids such as a trichloroisocyanuric acid, a tribromoisocyanuric acid, a dichloroisocyanuric acid, a sodium dichloroisocyanurate, a potassium dichloroisocyanurate, a calcium dichloroisocyanurate, a magnesium dichloroisocyanurate or hydrates thereof; chlorine, bromine; metal salts of alkali hypochlorite such as sodium hypochlorite, etc.; and alkaline earth metal salts of hypochlorous acid such as a calcium hypochloride, etc., which will be used in an amount of 0.5 to 1.5 equivalents and, preferably, in an amount of 0.8 to 1.2 equivalents per equivalent of the starting 4,5-bis(hydroxymethyl) imidazole compound.

When the halogenating agent is used in an amount of smaller than 0.5 equivalent per equivalent of the starting 4,5-bis(hydroxymethyl) imidazole compound, the unreacted starting material remains in large amounts. When the halogenating agent is used in an amount greater than 1.5 equivalents, on the other hand, the 4,5-dihaloimidazole compound is formed in large amounts, which is not desirable.

The solvent used for the process of the present invention may be water. It is, however, desired to use an organic solvent which dissolves the starting 4,5-bis(hydroxymethyl) imidazole compound but does not react with the halogenating agent such as N-chlorosuccinimide. Representative examples of the organic solvent include alcohols such as methanol, ethanol, etc., ethers such as tetrahydrofurane, 1,4-dioxane, etc. and chlorinated hydrocarbons such as methylene chloride, chloroform, etc.

Among the 4-chloro-5-(hydroxymethyl) imidazole compounds synthesized by the process of the present invention, the following compounds are novel compounds which have not yet been prepared, i.e., a 2-methyl-4-chloro-5-(hydroxymethyl) imidazole, a 2-ethyl-4-chloro-5-(hydroxymethyl) imidazole, a 2-isopropyl-4-chloro-5-(hydroxymethyl) imidazole and a 2-undecyl-4-chloro-5-(hydroxymethyl) imidazole. These 4-chloro-5-(hydroxymethyl) imidazole compounds exhibit the following properties.

2-Methyl-4-chloro-5-(hydroxymethyl) imidazole:

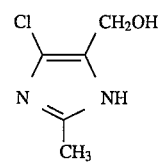

Colorless powder, m.p., 166°–167° C.
TLC (silica gel-acetone): Rf 0.42
IR(KBr): v3100, 1600, 1527, 1414, 1366, 1244, 1230, 1217, 1110, 1038, 1023, 1008, 784 cm$^{-1}$
NMR($d_4$-methanol): δ4.47(s,2H), 2.29(s,3H) MS: m/e 146 ($M^+$)

2-Ethyl-4-chloro-5-(hydroxymethyl) imidazole

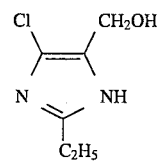

Colorless crystal, m.p., 134°–136° C.
TLC (silica gel-acetone): Rf 0.69
IR(KBr): v3080, 1600, 1516, 1450, 1430, 1392, 1355, 1323, 1272, 1240, 1220, 1110, 1067, 1010, 960, 850, 774, 710, 680 cm$^{-1}$
NMR($d_4$-methanol): δ4.49(s,2H), 2.65(q,2H,J=8 Hz), 1.25(t,3H,J=8 Hz)
MS: m/e 160($M^+$)

2-isopropyl-4-chloro-5-(hydroxymethyl) imidazole

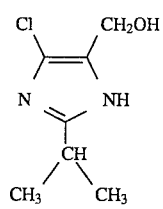

Colorless crystal, m.p., 170°–176° C.
TLC (silica gel-acetonr): Rf 0.72
IR(KBr): v7 2980, 1600, 1514, 1450, 1395, 1366, 1327, 1305, 1265, 1244, 1220, 1160, 1105, 1094, 1010, 840, 767, 725 cm$^{-1}$
NMR($d_4$-methanol): δ4.48(s,2H), 2.95(m,1H), 1.27 (d, 6H, J=7 Hz )
MS: m/e 174 ($M^+$)

2-Undecyl-4-chloro-5-(hydroxymethyl) imidazole

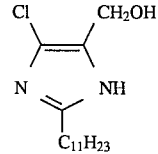

Colorless crystal, m.p., 103°–114° C.
TLC (silica gel-ethyl acetate): Rf 0.56
IR(KBr): v3140, 3090, 2920, 2860 1600, 1520, 1470, 1455, 1425, 1234, 1110, 998, 850, 796, 712 cm$^{-1}$
NMR($d_4$-methanol): δ4.47(s,2H) , 2.61(t,2H,J=8 Hz), 1.59(m,2H), 1.28(br.s, 16H), 0.89(t,3H,J=6 Hz)
MS: m/e 286 ($M^+$)

EXAMPLES

The invention will now be concretely described by way of Examples.

EXAMPLE 1

1.45 Grams (10.9 mmol) of an N-chlorosuccinimide was added to a solution consisting of 1.91 g (10.4 mmol) of a 2-butyl-4,5-bis(hydroxymethyl) imidazole, 100 ml of ethanol and 40 ml of 1,4-dioxane maintained at room temperature. The mixture was reacted for 18 hours with stirring and, then, the solvent was distilled off under reduced pressure. The resulting reaction product was washed with water and was recrystallized from acetonitrile to obtain a pale yellowish scale-like crystalline 2-butyl-4- chloro-5-(hydroxymethyl) imidazole in an amount of 1.00 g (yield, 51%). Recrystallization was further effected with acetonitrile to obtain the milk-white crystalline compound in pure form.

The thus obtained 2-butyl-4-chloro-5-(hydroxymethyl) imidazole exhibited TLC and spectra as follows:
Milk-white crystal, m.p., 141°–147° C.
TLC (silica gel-acetone): Rf 0.73
IR(KBr): ν2975, 1598, 1524, 1456, 1392, 1355, 1304, 1284, 1269, 1240, 1222, 1106, 1023, 860, 800, 726, 715 cm$^{-1}$
NMR($d_4$-methanol): δ4.48(s,2H), 2.62(t,2H,J=7 Hz), 1.82–1.16(m,4H), 0.94(t,3H,J=6 Hz)
MS: m/e 188(M$^+$)

EXAMPLE 2

3.86 Grams (28.9 mmol) of the N-chlorosuccinimide was added little by little to a solution consisting of 3.87 g (27.2 mmol) of a 2-methyl-4,5-bis(hydroxymethyl) imidazole and 50 ml of water maintained at room temperature with stirring over a period of about 40 minutes. The mixture was then stirred at the same temperature for 20 hours followed by the addition of sodium carbonate thereto to make the mixture alkaline. Water was then distilled off under reduced pressure. The resulting reaction mixture was extracted with ethanol, and the extract was evaporated dryness under reduced pressure. The resulting solid product was then extracted with acetone and the extract was evaporated under reduced pressure to obtain a yellowish oily product. The oily product was then subjected to the column chromatography (silica gel-acetone) to obtain a yellowish brown crystalline 2-methyl-4-chloro-5-(hydroxymethyl) imidazole in an amount of 2.4 g (yield, 60.2%). By using acetonitrile, the recrystallization was repeated two times to obtain a colorless powdery product in pure form. The TLC and spectra of this compound were the same as the properties exhibited by the above-mentioned 2-methyl-4-chloro-5-(hydroxymethyl) imidazole.

EXAMPLE 3

1.76 Grams (13.2 mmol) of the N-chlorosuccinimide was added little by little to a solution consisting of 2.06 g (13.2 mmol) of an ethyl-4,5-bis(hydroxymethyl) imidazole, 100 ml of ethanol and 40 ml of 1,4-dioxane maintained at room temperature with stirring over a period of about 11 minutes. The mixture was then stirred at the same temperature for three hours and for another 30 minutes at a temperature of 50° C. After the reaction, the solvent was distilled off under reduced pressure and the resulting yellowish oily product was subjected to the column chromatography (silica gel-acetone), and the obtained effluent was evaporated to dryness under reduced pressure. By using acetonitrile, the resulting solid product was recrystallized three times to obtain a colorless crystalline 2-ethyl-4-chloro-5-(hydroxymethyl) imidazole in an amount of 0.82 g (yield, 39.0%). The TLC and spectra of this compound were the same as the properties exhibited by the above-mentioned 2-ethyl-4-chloro-5-(hydroxymethyl) imidazole.

EXAMPLE 4

2.81 Grams (21 mmol) of the N-chlorosuccinimide was added little by little to a solution consisting of 3.47 g (20.4 mmol) of a 2-isopropyl-4,5-bis(hydroxymethyl) imidazole and 220 ml of ethanol at a temperature of 40° to 45° C. with stirring over a period of about 25 minutes. The mixture was stirred at the same temperature for two hours to effect the reaction, and then ethanol was distilled off under reduced pressure. The resulting reaction product was washed with water to obtain a pale yellowish powdery crystalline 2-isopropyl-4-chloro-5-(hydroxymethyl) imidazole in an amount of 1.69 g (yield, 47.4%). By using acetonitrile, the recrystallization was effected twice to obtain a colorless crystalline product in pure form. The TLC and spectra of this compound were the same as the properties exhibited by the above-mentioned 2-isopropyl-4-chloro-5-(hydroxymethyl) imidazole.

EXAMPLE 5

1.10 Grams (8.3 mmol) of the N-chlorosuccinimide was added little by little to a solution consisting of 2.15 g (7.6 mmol) of a 2-undecyl-4,5-bis(hydroxymethyl) imidazole and 200 ml of ethanol at a temperature of 40° to 45° C. over a period of about 23 minutes. The mixture was stirred at the same temperature for two hours to effect the reaction and, then, ethanol was distilled off under reduced pressure. The resulting reaction product was washed with water and was then recrystallized from acetone to obtain a creamy-white fine crystalline 2-undecyl-4-chloro-5-(hydroxymethyl) imidazole in an amount of 1.16 g (yield, 53.1%). By using acetonitrile, furthermore, the recrystallization was effected twice to obtain a colorless crystalline product in pure form. The TLC and spectra of this compound were the same as the properties exhibited the above-mentioned 2-undecyl-4-chloro-5-(hydroxymethyl) imidazole.

EXAMPLE 6

1.53 Grams (6.6 mmol) of trichloroisocyanuric acid was added little by little to a solution consisting of 2.03 g (13 mmol) of the 2-ethyl-4,5-bis(hydroxymethyl) imidazole, 100 ml of ethanol and 40 ml of 1,4-dioxane at room temperature with stirring over a period of about 10 minutes. The mixture was stirred at the same temperature for one hour, the solvent was distilled off under reduced pressure, the reaction product was extracted with ethanol, and the extract was evaporated to dryness under reduced pressure. The resulting solid product was then extracted with acetone, the extract was concentrated and was then subjected to the column chromatography (silica gel-acetone), and the effluent was further concentrated and was recrystallized from acetonitrile to obtain a 2-ethyl-4-chloro-5-(hydroxymethyl) imidazole in an amount of 0.78 g (yield, 37.4%). The TLC and spectra were measured to be the same as those of Example 3.

EXAMPLE 7

11.5 Grams (15 mmol) of an aqueous solution containing 9.7% of sodium hypochlorite was dropwisely added to a solution consisting of 2.53 g (16.2 mmol) of the 2-ethyl-4, 5-bis(hydroxymethyl) imidazole and 50 ml of water. After the dropwise addition has been finished, the mixture was stirred at room temperature for one hour, followed by neutralization by the addition of dry ice and further followed by evaporation to dryness under reduced pressure. The resulting solid was extracted with ethanol, the extract was evaporated under reduced pressure, and the resulting solid product was extracted with acetone. 1.48 Grams of the starting 2-ethyl-4,5-bis(hydroxymethyl) imidazole was recovered as an extraction residue, the extract was concentrated under reduced pressure, and was subjected to the column chromatography (silica gel-acetone) to obtain a 2-ethyl-4-chloro-5-(hydroxymethyl) imidazole in an amount of 0.46 g (yield 43.0% with respect to the starting material consumed). The TLC and spectra were measured to be the same as those of Example 3.

EXAMPLE 8

26.3 Grams (15.6 mmol) of a 4.2% chlorine-carbon tetrachloride solution was dropwisely added to a solution consisting of 2.52 g (14.8 mmol) of the 2-isopropyl- 4,5-bis(hydroxymethyl) imidazole and 200 ml of ethanol maintaining a temperature of 40° C. with stirring. After the dropwise addition has been finished, the stirring was continued at 40° C. for one hour and, then, the solvent was distilled off under reduced pressure. After the residual brown oil was dissolved in water, sodium carbonate was added thereto to make the mixture alkaline. The mixture was evaporated again under reduced pressure. The obtained resulting solid product was extracted with ethanol, the extract was evaporated under reduced pressure, and the resulting solid product was extracted with cold water. 0.71 Grams of the starting 2-isopropyl-4,5-bis(hydroxymethyl) imidazole was recovered as the extraction residue, and the extract after evaporate under reduced pressure was subjected to the column chromatography (silica gel-acetone) to obtain a 2-isopropyl-4-chloro-5-(hydroxymethyl) imidazole in an amount of 0.56 g (yield, 30.3% with respect to the starting material consumed). By using acetonitrile, the compound was further refined. The TLC and spectra of this compound were measured to be the same as those of Example 4.

EXAMPLE 9

2.4 Grams (10.9 mmol) of sodium dichloroisocyanurate was added to a solution consisting of 3.68 g (20 mmol) of the 2-butyl-4,5-bis(hydroxymethyl) imidazole, 40 ml of ethanol and 15 ml of dioxane maintained at a temperature of 40° to 45° C. with stirring. The mixture was further stirred at a temperature of 40° to 60° C. for two hours. The obtained reaction solution was cooled, filtered to separate impurities, the filtrate was concentrated under reduced pressure. The resulting residue product was washed with water, and was recrystallized twice from acetonitrile to obtain a pale yellowish crystalline 2-butyl-4-chloro-5-(hydroxymethyl) imidazole in an amount of 1.60 g yield, (42.5%).

EXAMPLE 10

2.56 Grams (10 mmol) of a sodium dichloroisocyanurate dihydrate was added to a solution consisting of 3.68 g (20 mmol) of the 2-butyl-4,5-bis(hydroxymethyl) imidazole, 40 ml of ethanol and 15 ml of dioxane maintained at a temperature of 40° to 45° C. with stirring. The mixture was further stirred at a temperature of 50° to 60° C. for three hours. The obtained reaction solution was cooled, filtered to separate impurities, the filtrate was concentrated under reduced pressure. The resulting residue product was washed with water and was recrystallized twice from acetonitrile to obtain a pale yellowish crystalline 2-butyl-4-chloro-5-(hydroxymethyl) imidazole in an amount of 1.90 g (yield, 50%).

EXAMPLE 11

3.56 Grams (20 mmol) of the N-bromosuccinimide was added to a solution consisting of 3.68 g (20.0 mmol) of the 2-butyl-4,5-bis(hydroxymethyl) imidazole, 40 ml of ethanol and 15 ml of dioxane maintained at a temperature of 45° to 50° C. with stirring. The mixture was further reacted at the same temperature for 30 minutes with stirring, and then the solvent was distilled off under reduced pressure. The obtained reaction product was washed with water and was recrystallized from acetonitrile to obtain a pale yellowish scale-like crystalline 2-butyl-4-bromo-5-(hydroxymethyl) imidazole in an amount of 2.36 g (yield, 51%).

EXAMPLE 12

3.56 Grams (20 mmol) of the N-bromosuccinimide was added to a solution consisting of 4.86 g (20 mmol) of the 2-benzyl-4,5-bis(hydroxymethyl) imidazole, 80 mol of methoxyethanol and 30 ml of dioxane maintained at a temperature of 45° to 50° C. with stirring. The mixture was further reacted at the same temperature for 24 hours with stirring and, then, the solvent was distilled off under reduced pressure. The obtained reaction product was washed with water and was recrystallized from acetonitrile to obtain a 2-benzyl-4-bromo-5-(hydroxymethyl) imidazole in an amount of 2.1 g (yield, 39%).

EXAMPLE 13

2.34 Grams (17.5 mmol) of the N-chlorosuccinimide was added to a solution consisting of 3.26 g (16 mmol) of the 2-phenyl-4,5-bis(hydroxymethyl) imidazole, 24 ml of methoxyethanol and 37 ml of dioxane maintained at a temperature of 50° C. with stirring. The mixture was then reacted at the same temperature for 24 hours with stirring, and the reaction solution was concentrated under reduced pressure. The obtained reaction product was washed with water and was recrystallized from propyl alcohol to obtain a 2-phenyl-4-chloro-5-(hydroxymethyl) imidazole in an amount of 1.0 g (yield 30%).

The present invention simplifies the steps for preparing 4-halo-5-(hydroxymethyl) imidazole compounds that can be effectively used as intermediates for medicines, and uses the starting material which is relatively cheap and can be easily handled. Therefore, the present invention lends itself well for the production on an industrial scale.

We claim:

1. A process for synthesizing a 4-chloro-5-(hydroxymethyl) imidazole compound represented by the following formula

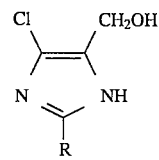

wherein

R is a hydrogen atom, an alkyl group, an aryl group or an aralkyl group, which comprises reacting a 4,5-bis(hydroxymethyl) imidazole compound with a chlorinating agent.

2. A process according to claim 1, wherein the chlorinating agent is an N-chlorosuccinimide.

3. A process according to claim 1, wherein the haloge nating agent is a chlorinated isocyanuric acid compound.

4. A process according to claim 1, wherein the chlorinating agent is a sodium dichloroisocyanurate.

* * * * *